(12) United States Patent
Patel et al.

(10) Patent No.: US 7,488,298 B2
(45) Date of Patent: *Feb. 10, 2009

(54) INTEGRATED LANCING TEST STRIP WITH CAPILLARY TRANSFER SHEET

(75) Inventors: Paul Patel, Sunnyvale, CA (US); Edward P. Perez, Redwood City, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 553 days.

This patent is subject to a terminal disclaimer.

(21) Appl. No.: 10/961,640

(22) Filed: Oct. 8, 2004

(65) Prior Publication Data

US 2006/0079810 A1    Apr. 13, 2006

(51) Int. Cl.
*A61B 5/00* (2006.01)
*B65D 81/00* (2006.01)

(52) U.S. Cl. .................. 600/584; 600/573; 600/576; 600/578; 600/583

(58) Field of Classification Search ............... 600/573, 600/576, 583–584, 578
See application file for complete search history.

(56) References Cited

U.S. PATENT DOCUMENTS

| | | | |
|---|---|---|---|
| 1,328,459 | A | 1/1920 | Smith |
| 2,359,550 | A | 10/1944 | Eriksen |
| 2,646,799 | A | 7/1953 | Jacoby, Jr. |
| 2,801,633 | A | 8/1957 | Ehrlich |
| 2,866,542 | A | 12/1958 | Svirchev |
| 2,998,880 | A | 9/1961 | Ladd |
| 3,604,616 | A | 9/1971 | Greif |
| 3,669,256 | A | 6/1972 | Jacob |
| 3,802,842 | A | 4/1974 | Lange et al. |
| D234,644 | S | 3/1975 | Sugiyama et al. |
| 3,910,455 | A | 10/1975 | Ferraro |

(Continued)

FOREIGN PATENT DOCUMENTS

CA    2287757    4/2001

(Continued)

OTHER PUBLICATIONS

Haar et al., U.S. Appl. No. 12/037,197, filed Feb. 26, 2008, "Assembly for Receiving Body Fluids, and Method for the Production Thereof".

(Continued)

*Primary Examiner*—Max Hindenburg
*Assistant Examiner*—Rene Towa
(74) *Attorney, Agent, or Firm*—Woodard, Emhardt, Moriarty, McNett & Henry LLP (57) ABSTRACT

An integrated bodily fluid sampling device includes a lancet, a test strip attached to the lancet, and a flexible sheet extending from the test strip. The lancet and the flexible sheet form a gap sized to draw bodily fluid onto the test strip via capillary action. Further, a sampling end portion of the flexible sheet is shaped to enhance capillary action of the sheet. In one form, a removable film covers the lancet and forms a seal with the flexible sheet such that the seal surrounds a lancet tip. In another form, an insulating layer covers a portion of the lancet to prevent electrical interference between the lancet and an electrical testing system on the test strip and ensure an accurate analysis of the bodily fluid.

39 Claims, 5 Drawing Sheets

U.S. PATENT DOCUMENTS

| | | | |
|---|---|---|---|
| 3,942,634 A | 3/1976 | Gandi et al. | |
| 3,967,728 A | 7/1976 | Gordon et al. | |
| 4,061,468 A | 12/1977 | Lange et al. | |
| 4,095,589 A | 6/1978 | Manschot et al. | |
| 4,123,840 A | 11/1978 | Rumer, Jr. | |
| D254,444 S | 3/1980 | Levine | |
| 4,203,446 A | 5/1980 | Hofert et al. | |
| 4,360,016 A | 11/1982 | Sarrine | |
| 4,375,815 A | 3/1983 | Burns | |
| 4,385,692 A | 5/1983 | Eldridge, Jr. | |
| 4,462,405 A | 7/1984 | Ehrlich | |
| 4,469,110 A | 9/1984 | Siama | |
| 4,490,465 A | 12/1984 | Limbach et al. | |
| 4,506,787 A | 3/1985 | Bruso | |
| 4,597,493 A | 7/1986 | Bruso | |
| 4,627,445 A | 12/1986 | Garcia et al. | |
| 4,635,488 A * | 1/1987 | Kremer | 73/864.72 |
| 4,637,403 A | 1/1987 | Garcia et al. | |
| 4,653,513 A | 3/1987 | Dombrowski | |
| 4,677,979 A | 7/1987 | Burns | |
| 4,787,398 A | 11/1988 | Garcia et al. | |
| 4,790,979 A | 12/1988 | Terminiello et al. | |
| 4,869,249 A | 9/1989 | Crossman et al. | |
| 4,873,993 A * | 10/1989 | Meserol et al. | 600/573 |
| 4,895,147 A | 1/1990 | Bodicky et al. | |
| 4,915,697 A | 4/1990 | DuPont | |
| 4,924,879 A | 5/1990 | O'Brien | |
| 4,990,154 A | 2/1991 | Brown et al. | |
| 4,997,092 A | 3/1991 | Dupont | |
| 5,035,704 A | 7/1991 | Lambert et al. | |
| 5,100,391 A | 3/1992 | Schutte et al. | |
| 5,129,511 A * | 7/1992 | Brown et al. | 206/63.3 |
| 5,260,031 A * | 11/1993 | Seymour | 422/101 |
| 5,304,193 A | 4/1994 | Zhadanov | |
| 5,406,939 A | 4/1995 | Bala | |
| 5,409,133 A | 4/1995 | Gringer | |
| 5,423,847 A | 6/1995 | Strong et al. | |
| 5,529,581 A | 6/1996 | Cusack | |
| 5,540,709 A | 7/1996 | Ramel | |
| 5,545,173 A | 8/1996 | Herbst | |
| 5,582,184 A | 12/1996 | Erickson et al. | |
| 5,607,401 A | 3/1997 | Humphrey | |
| 5,607,437 A | 3/1997 | Simon et al. | |
| 5,613,978 A | 3/1997 | Harding | |
| 5,628,764 A | 5/1997 | Schraga | |
| 5,628,765 A | 5/1997 | Morita | |
| 5,699,907 A | 12/1997 | Langenstuck | |
| 5,699,909 A | 12/1997 | Foster | |
| 5,730,753 A | 3/1998 | Morita | |
| RE35,803 E | 5/1998 | Lange et al. | |
| 5,755,733 A | 5/1998 | Morita | |
| 5,776,719 A | 7/1998 | Douglas et al. | |
| 5,795,632 A | 8/1998 | Buchalter | |
| 5,798,031 A | 8/1998 | Charlton et al. | |
| 5,824,491 A | 10/1998 | Priest et al. | |
| 5,830,225 A | 11/1998 | Detsch | |
| 5,857,983 A | 1/1999 | Douglas et al. | |
| 5,871,494 A | 2/1999 | Simons et al. | |
| 5,873,887 A | 2/1999 | King et al. | |
| 5,879,311 A | 3/1999 | Duchon et al. | |
| 5,916,230 A | 6/1999 | Brenneman et al. | |
| 5,931,846 A | 8/1999 | Simon et al. | |
| 5,951,492 A | 9/1999 | Douglas et al. | |
| 5,951,493 A | 9/1999 | Douglas et al. | |
| 5,962,215 A | 10/1999 | Douglas et al. | |
| 5,964,718 A | 10/1999 | Duchon et al. | |
| 5,971,941 A | 10/1999 | Simons et al. | |
| 5,984,940 A | 11/1999 | Davis et al. | |
| 5,997,561 A | 12/1999 | Bocker et al. | |
| 6,010,519 A | 1/2000 | Mawhirt et al. | |
| 6,022,366 A | 2/2000 | Schraga | |
| 6,036,659 A | 3/2000 | Ray et al. | |
| 6,036,924 A | 3/2000 | Simons et al. | |
| 6,045,497 A | 4/2000 | Schweich et al. | |
| 6,045,567 A | 4/2000 | Taylor et al. | |
| 6,048,352 A | 4/2000 | Douglas et al. | |
| 6,051,293 A | 4/2000 | Weilandt | |
| 6,056,701 A | 5/2000 | Duchon et al. | |
| 6,066,103 A | 5/2000 | Duchon et al. | |
| 6,071,250 A | 6/2000 | Douglas et al. | |
| 6,071,294 A | 6/2000 | Simons et al. | |
| 6,086,545 A | 7/2000 | Roe et al. | |
| 6,099,484 A | 8/2000 | Douglas et al. | |
| 6,143,164 A * | 11/2000 | Heller et al. | 600/583 |
| 6,156,050 A | 12/2000 | Davis et al. | |
| 6,156,051 A | 12/2000 | Schraga | |
| 6,159,424 A | 12/2000 | Kauhaniemi et al. | |
| 6,183,489 B1 | 2/2001 | Douglas et al. | |
| 6,210,421 B1 | 4/2001 | Bocker et al. | |
| 6,258,229 B1 | 7/2001 | Winarta et al. | |
| 6,270,637 B1 * | 8/2001 | Crismore et al. | 204/403.04 |
| 6,283,982 B1 | 9/2001 | Levaughn et al. | |
| 6,299,607 B1 | 10/2001 | Osborn, III et al. | |
| 6,306,152 B1 | 10/2001 | Verdonk et al. | |
| 6,315,738 B1 | 11/2001 | Nishikawa et al. | |
| 6,319,210 B1 | 11/2001 | Douglas et al. | |
| 6,332,871 B1 | 12/2001 | Douglas et al. | |
| 6,346,114 B1 | 2/2002 | Schraga | |
| 6,349,229 B1 | 2/2002 | Watanabe et al. | |
| 6,352,514 B1 | 3/2002 | Douglas et al. | |
| 6,364,890 B1 | 4/2002 | Lum et al. | |
| 6,409,740 B1 | 6/2002 | Kuhr et al. | |
| 6,419,661 B1 | 7/2002 | Kuhr et al. | |
| 6,561,989 B2 * | 5/2003 | Whitson | 600/573 |
| 6,612,111 B1 | 9/2003 | Hodges et al. | |
| 6,706,159 B2 | 3/2004 | Moerman et al. | |
| 6,707,554 B1 | 3/2004 | Miltner et al. | |
| 6,800,488 B2 * | 10/2004 | Khan et al. | 436/166 |
| 6,866,675 B2 | 3/2005 | Perez et al. | |
| 7,008,799 B1 | 3/2006 | Zimmer et al. | |
| 7,211,052 B2 | 5/2007 | Roe | |
| 7,264,627 B2 | 9/2007 | Perez | |
| 7,322,942 B2 * | 1/2008 | Roe | 600/583 |
| 2001/0027277 A1 | 10/2001 | Klitmose | |
| 2001/0027327 A1 | 10/2001 | Schraga | |
| 2001/0037099 A1 | 11/2001 | Effenhauser | |
| 2001/0039387 A1 | 11/2001 | Rutynowski et al. | |
| 2002/0002344 A1 | 1/2002 | Douglas et al. | |
| 2002/0004196 A1 | 1/2002 | Whitson | |
| 2002/0016006 A1 | 2/2002 | Wendelbo et al. | |
| 2002/0029059 A1 | 3/2002 | Purcell | |
| 2002/0040230 A1 | 4/2002 | Kuhr et al. | |
| 2002/0052618 A1 | 5/2002 | Haar et al. | |
| 2002/0082522 A1 | 6/2002 | Douglas et al. | |
| 2002/0103499 A1 | 8/2002 | Perez et al. | |
| 2002/0137998 A1 | 9/2002 | Smart et al. | |
| 2002/0160520 A1 | 10/2002 | Orloff et al. | |
| 2002/0168290 A1 | 11/2002 | Yuzhakov et al. | |
| 2002/0177761 A1 | 11/2002 | Orloff et al. | |
| 2002/0177763 A1 | 11/2002 | Burns et al. | |
| 2002/0177788 A1 | 11/2002 | Hodges | |
| 2003/0018282 A1 | 1/2003 | Effenhauser et al. | |
| 2003/0028087 A1 | 2/2003 | Yuzhakov et al. | |
| 2003/0028125 A1 | 2/2003 | Yuzhakov et al. | |
| 2003/0050573 A1 | 3/2003 | Kuhr et al. | |
| 2003/0060730 A1 | 3/2003 | Perez | |
| 2003/0073932 A1 | 4/2003 | Varey | |
| 2003/0144608 A1 | 7/2003 | Kojima et al. | |
| 2003/0196894 A1 | 10/2003 | Cai et al. | |
| 2003/0199744 A1 | 10/2003 | Buse et al. | |
| 2003/0211619 A1 | 11/2003 | Olson et al. | |
| 2003/0212344 A1 | 11/2003 | Yuzhakov et al. | |
| 2003/0212346 A1 | 11/2003 | Yuzhakov et al. | |
| 2004/0034318 A1 | 2/2004 | Fritz et al. | |

| | | |
|---|---|---|
| 2004/0055898 A1 | 3/2004 | Heller et al. |
| 2004/0064068 A1 | 4/2004 | DeNuzzio et al. |
| 2004/0106941 A1 | 6/2004 | Roe |
| 2004/0127818 A1 | 7/2004 | Roe et al. |
| 2004/0127819 A1 | 7/2004 | Roe et al. |
| 2004/0127929 A1 | 7/2004 | Roe |
| 2004/0186394 A1* | 9/2004 | Roe et al. ............ 600/583 |
| 2005/0021066 A1 | 1/2005 | Kuhr et al. |
| 2005/0245954 A1 | 11/2005 | Roe et al. |
| 2005/0251064 A1 | 11/2005 | Roe |
| 2005/0277850 A1 | 12/2005 | Mace et al. |
| 2005/0283094 A1 | 12/2005 | Thym et al. |
| 2006/0008389 A1 | 1/2006 | Sacherer et al. |
| 2006/0079810 A1 | 4/2006 | Patel et al. |
| 2006/0100542 A9 | 5/2006 | Wong et al. |
| 2006/0100543 A1 | 5/2006 | Raney et al. |
| 2006/0174592 A1 | 8/2006 | Chan |
| 2006/0200045 A1 | 9/2006 | Roe |
| 2006/0229532 A1 | 10/2006 | Wong et al. |
| 2006/0293611 A1 | 12/2006 | Calasso |
| 2007/0016103 A1 | 1/2007 | Calasso |
| 2007/0038149 A1 | 2/2007 | Calasso |
| 2007/0167869 A1 | 7/2007 | Roe |
| 2007/0173739 A1 | 7/2007 | Chan |
| 2007/0173740 A1 | 7/2007 | Chan et al. |
| 2007/0191738 A1 | 8/2007 | Raney |
| 2007/0191739 A1 | 8/2007 | Roe |
| 2008/0097244 A1 | 4/2008 | Arnitz |
| 2008/0103415 A1 | 5/2008 | Roe et al. |
| 2008/0161724 A1 | 7/2008 | Roe |

FOREIGN PATENT DOCUMENTS

| | | | |
|---|---|---|---|
| DE | 197 53 847 A1 | 6/1999 |
| EP | 0 582 276 A1 | 2/1994 |
| EP | 1 281 352 A1 | 2/2003 |
| JP | 2000-116768 A2 | 4/2000 |
| WO | WO 93/09710 A1 | 5/1993 |
| WO | WO 93/09723 A1 | 5/1993 |
| WO | WO00/40150 | 7/2000 |
| WO | WO 01/72220 A1 | 10/2001 |
| WO | WO 02/26129 A1 | 4/2002 |
| WO | WO 02/36010 A1 | 5/2002 |
| WO | WO 02/056751 A2 | 7/2002 |
| WO | WO 03/015627 A3 | 2/2003 |
| WO | WO 2004/060174 A2 | 7/2004 |
| WO | 2004064636 A1 | 8/2004 |
| WO | 2004086970 A1 | 10/2004 |
| WO | 2005084530 A2 | 9/2005 |
| WO | 2005084545 A1 | 9/2005 |
| WO | 2005084546 A2 | 9/2005 |
| WO | 2005104948 A1 | 11/2005 |
| WO | 2006005503 A1 | 1/2006 |
| WO | 2007147494 A2 | 12/2007 |

OTHER PUBLICATIONS

Haar et al., U.S. Appl. No. 12/105,596, filed Apr. 18, 2008, "Analytical System for Detecting An Analyte in a Body Fluid And Disposable Integrated Puncturing and Analyzing Element".

Joseph et al., U.S. Appl. No. 12/180,101, filed Jul. 25, 2008, Method for Manufacturing a Sterilized Lancet Integrated Biosensor.

Wong et al., U.S. Appl. No. 12/020,766, filed Jan. 28, 2008, "Rapid Blood Expression and Sampling".

Joseph et al., U.S. Appl. No. 12/177,328, filed Jul. 22, 2008, "Method and Apparatus for Lighted Test Strip".

* cited by examiner

INTEGRATED LANCING TEST STRIP WITH CAPILLARY TRANSFER SHEET

BACKGROUND OF THE INVENTION

The present invention generally relates to integrated lancing test strips, and more specifically, but not exclusively, concerns an integrated lancing test strip with a hydrophilic sheet or flag that is shaped and structured to enhance fluid flow into the test strip as well as maintain the sterility of the test strip.

Body fluid sampling devices have been developed to draw body fluid, such as blood or interstitial fluid, from a person or animal and analyze the drawn fluid for any number of characteristics, such as blood glucose levels for diabetics. Many of these devices have been designed for home based monitoring so that an individual can monitor their condition throughout the day. In a conventional procedure, the medical practitioner or the individual first creates an incision in the skin by lancing the subject's skin with a lancet. To avoid infection of the incision site and/or contamination of the fluid collected, the lancet is sterilized and packaged in a sterile manner prior to use. Typical packaging of the lancet involves covering the tip of the lancet with a protective cap that maintains the sterility of the lancet as wells prevents subjects from accidentally cutting themselves or others with the lancet. Maintaining the sterility of the lancet while at the same time providing for ease in removal of the protective cap can be difficult, especially when the test is self-administered. Usually, the subject is either elderly or otherwise has some infirmity that reduces their hand dexterity, which in turn makes removal of the cap difficult. One solution has been to weaken the connection between the cap and the lancet, but by weakening this connection, the protective caps are more prone to be dislodged during shipping. Complicated systems have been developed to automatically remove the caps, but the caps still tend to be bulky in nature, which makes storage and disposal of the discarded caps problematic in the automatic system. Even with automatic systems, difficulties still exist in ensuring a consistent level of performance when removing the caps. Also, the bulky nature of the caps reduces the packing density of the lancets when attached together in a tape or cassette of lancets.

Usually, after lancing the skin, the individual has to manually position a test strip or a capillary tube in the drop of body fluid, but as mentioned before, this task can be difficult for many individuals, such as the elderly. The ability to draw a sufficient amount of fluid onto the test strip is always a concern, especially with home-based testing systems. When the amount of fluid is insufficient, the individual can become frustrated by having to repeatedly perform the test and waste multiple test strips. For example, if the individual is unable to steadily hold the test strip, the test strip may not collect a sufficient amount of fluid for a reliable test. Also, the user can press the test strip or the sampling device to hard against the skin so that the incision closes, thereby prematurely cutting off the fluid supply. Wicking structures have been developed to help draw fluid onto the test strip or into a capillary tube. However, it has been discovered that these wicking structures have a number of significant drawbacks. For instance, the wicking structures tend to waste fluid by requiring that a considerable amount of the fluid be absorbed by the wicking structure before transporting the fluid to the testing area on the test strip. Also, typical wicking structures are predisposed to smear the droplet of blood or other fluid on the skin, which in turn tends to waste fluid.

After the body fluid sample is collected, the sample may be analyzed for a variety of characteristics through optical and/or electrochemical analysis as well as in other manners. Integrated lancing test strips have been recently developed in which a lancet is attached to a test strip or some other type of testing media, such that the single, integrated unit can both draw and analyze body fluid. Typically, the lancet is made of metal, such as surgical grade stainless steel. In most conventional body fluid sampling devices that use electrochemical test strips, metallic lancets do not significantly affect the readings from electrochemical test strips because the lancet and the electrochemical test strip are separate and spaced relatively far apart. However, with the advent of integrated lancing test strips, it has been discovered that the small spacing between the lancet and electrodes in the test strip can create considerable electrical interference, which can affect the readings generated from the test strip. The electrical interference becomes even more pronounced as the industry tends to shrink the integrated lancing test strips for incorporation into cassettes, cartridges and other types of storage units.

Thus, there remains the need for further improvement in this field.

SUMMARY

One aspect of the present invention concerns a device for sampling a body fluid from an incision in skin. The device includes a lancet, a test strip, and a fluid collection flag extending from the test strip for drawing bodily fluid to the test strip. Further, the fluid collection flag is flexible to bend during lancing and the fluid collection flag has a structure to minimize lateral wicking of the bodily fluid.

A further aspect concerns an integrated bodily fluid sampling device for sampling a bodily fluid from an incision in skin. The device includes a lancet with a lancet tip, a test strip coupled to the lancet, a fluid collection flag, and a protective film. The fluid collection flag extends from the test strip and the fluid collection flag draws bodily fluid onto the test strip. Further, the protective film detachably couples to the fluid collection flag to protect at least the lancet tip such that the lancet tip is sandwiched between the fluid collection flag and the film.

Another aspect concerns an integrated bodily fluid sampling device for sampling and testing a bodily fluid from an incision in skin. The device includes a lancet with a lancet tip, a test strip attached to the lancet, an insulating layer, and a fluid collection flag. The test strip has electrodes. Further, the insulating covers a portion of the lancet and prevents electrical interference between the lancet and the electrodes. The fluid collection flag is configured to draw bodily fluid onto the test strip.

Yet, another aspect concerns a method of drawing a body fluid. The method includes providing a sampling device with a fluid collection flag. The fluid collection flag is configured to minimize lateral wicking of the body fluid. The method also includes contacting a drop of the body fluid with the fluid collection flag and drawing the body fluid longitudinally along a length of the fluid collection flag with the fluid collection flag.

Another aspect concerns a method of providing a sampling device with a lancet that has a lancet tip to form an incision and a testing means to analyze body fluid from the incision. The method also includes sandwiching at least a lancet tip of the lancet between the protective film and a fluid collection flag to maintain sterility of the lancet tip. The fluid collection flag is configured to draw bodily fluid towards the testing means.

Further forms, objects, features, aspects, benefits, advantages, and embodiments of the present invention will become apparent from a detailed description and drawings provided herewith.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The present invention generally concerns an integrated lancing test strip that reduces the amount body fluid that needs to be drawn from an incision in tissue, such as skin. The device includes a lancet for forming the incision in the skin, a test strip or other testing device coupled to the lancet, and a flexible fluid collection sheet or flag extending from the test strip. After the lancet forms the incision, the fluid collection sheet is used to draw fluid from the incision into the test strip for analysis. The fluid collection sheet is made of flexible material so as to not close the incision when it contacts the skin, and the end of the collection sheet is shaped to reduce lateral wicking of the fluid as well smearing of the fluid, thereby increasing the amount of fluid directly transferred to the testing area in the test strip. In one form, the integrated lancing test strip includes a metallic lancet and electrodes with a reagent for analyzing the fluid. A portion of the lancet is coated or covered with a thin conformal film or coating that prevents electrical interference between the lancet and electrodes on the test strip. To maintain the sterility of the lancet, a protective, peelable film covers at least the tip of the lancet in one embodiment. An adhesive joins the peelable film to the fluid collection sheet such that the tip of the lancet is sandwiched in between.

Selected features from different embodiments of the present invention will be described with reference to integrated lancing test strips of the type illustrated in the drawings, but it should nevertheless be appreciated that these features can be incorporated into other types designs. As an non-limiting example, although the illustrated integrated lancing test strips have a lancet that is fixed relative to the rest of the test strip, it should be appreciated that the lancet or other portions of the test strip can be moveable relative to the rest of the test strip. Moreover, it is envisioned that multiple integrated lancing test strips can be stored or joined together in a cartridge and/or in a cassette. For other examples of integrated lancing test strip designs, please refer to commonly owned: U.S. patent application Ser. No. 10/767,522 to Roe et al.; U.S. patent application Ser. No. 10/330,724, filed Dec. 27, 2002 published as U.S. Patent Application Publication No. US 2004/0127818 A1 on Jul. 1, 2004; and U.S. patent application Ser. No. 10/308,463, filed Dec. 3, 2002, published as U.S. Patent Application Publication No. US 2004/0106941 A1 on Jun. 3, 2004, which are all hereby incorporated by reference in their entirety.

Figures 1, 2:
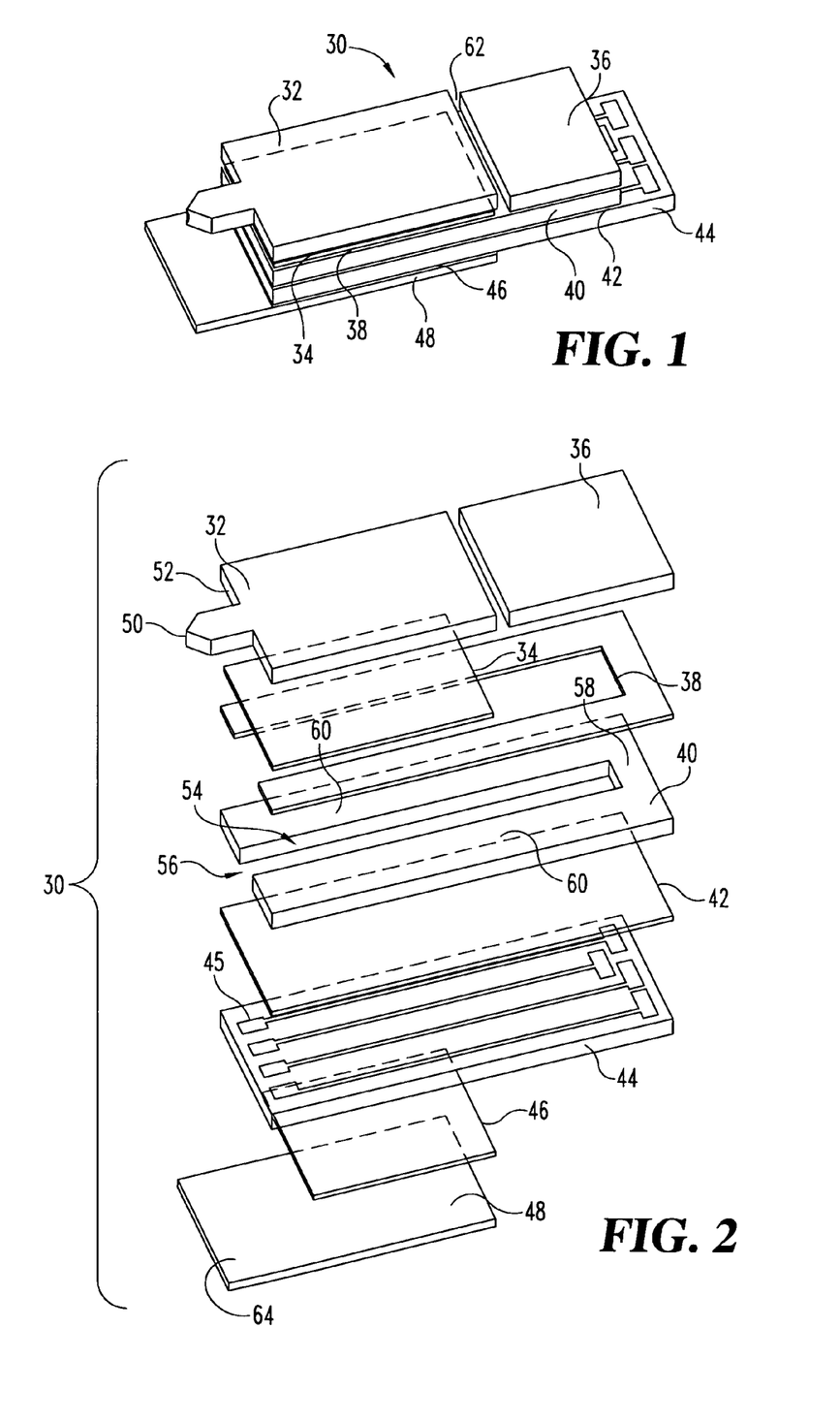
FIG. 1 is a perspective view of an integrated test strip according to one embodiment of the present invention.
FIG. 2 is an exploded view of the FIG. 1 test strip.

An integrated lancing test strip or disposable unit 30, according to one embodiment of the present invention, will now be described with reference to FIGS. 1 and 2. As shown in FIGS. 1 and 2, the device 30 includes an incision forming member or lancet 32 for forming an incision in tissue and an insulating layer 34 that covers at least a portion of the lancet 32 for electrically insulating the lancet 32 from the rest of the unit 30. A vent member 36 is spaced apart from the lancet 32, and a first layer of adhesive or adhesive tape 38 secures both the lancet 32 and the vent member 36 to a spacer 40. A second layer of adhesive 42 secures the spacer 40 to a test strip 44 with electrodes 45 that are used to analyze the fluid sample. On the side opposite the spacer 40, a third layer of adhesive 46 secures a fluid collection sheet or flag 48 to the test strip 44. The fluid collection sheet is used to draw a fluid sample into the unit 30. It should be recognized that the unit 30 can be used to manually or automatically lance an incision in tissue and analyze the fluid drawn from the incision. For the sake of clarity and brevity, other components used in conjunction with the unit 30 that are well known in the art, such as lancet drivers, and the like, that are not important to appreciate the present invention, will not be discussed in detail below.

In the illustrated embodiment, lancet 32 has a substantially flat shape. As should be appreciated, the lancet 32 can be various geometric shapes. For example, lancet 32 can be rounded. In this embodiment, the lancet 32 is made of metal, but it is contemplated that the lancet 32 can be made of other materials, such as plastic or ceramic, or a combination of materials, such as metal and plastic.

As shown in FIG. 2, the lancet 32 has a lancet tip or blade 50 extending from a guide edge 52 at one end of the lancet 32. As shown, the lancet tip 50 is substantially triangular in shape, however it should be appreciated that the lancet tip 50 can be various geometric shapes. The lancet tip 50 is configured to cut an incision into skin or other types of tissues and the guide edge 52 can be used to limit the penetration depth of the lancet tip 50 into the skin.

As mentioned previously, during the development of integrated lancing test strips, such as the one illustrated in FIGS.

1 and 2, it has been discovered that the lancet 32, especially when made of a conductive material such as metal, can interfere with the operation of the electrochemical test strip 44, due to their close proximity to one another. Even when the lancet 32 is made from insulative material, such as plastic, an electrostatic charge can sometimes still develop on the lancet 32 so as to interfere with the electrodes. Electrochemical techniques of analyzing body fluid generally rely upon the correlation between a charge-transfer or charge-movement property of the fluid sample (e.g., current, interfacial potential, impedance, conductance, and the like) and the concentration of the analyte, typically in conjunction with a reagent that produces or modifies charge-carriers when combined with the analyte that result in a reaction measurable by the electrodes on the test strip. Typically, a test system takes advantage of the reaction between the body fluid to be tested and the reagent present in the test system. It is theorized that the electrical interference created by the lancet 32 changes the impedance to the electrodes, which in turn affects the results from the test strip 44. In the illustrated embodiment, the insulating layer 34 is used to cover at least a portion of the lancet 32 in order to shield the test strip 44 from the undesirable electrical interference created by the lancet 32. The insulating layer 34 in the depicted embodiment generally conforms to the shape of the lancet 32, but it should be recognized that the insulating layer 34 can be shaped differently. It is also contemplated that the insulating layer 34 can be positioned at other locations between the lancet 32 and the test strip 44, while still shielding the test strip 44 from the undesirable interference created by the lancet 32. The insulating layer 34 can be made of various materials, such as aluminum oxide, polyparaxylene sold under the trademark PARALYENE™ or some other polymer or material, to name a few, that prevents electrical interference between the lancet 32 and electrodes 45 on the test strip 44. In the integrated lancing test strip 30, the insulating layer 34, the lancet 32, and the test strip 44 can be positioned even closer together than what was previously achievable without suffering the above-mentioned side affects, and thus, further miniaturization of the integrated lancing test strips 30 with electrochemical type test strips 44 is possible.

As should be further appreciated, the insulating layer 34 as well as other components of the unit 30 are assembled in an layer like fashion such that multiple integrated units 30 can be easily assembled in an continuous fashion. Continuous strips or layers of these components, such as the insulating layer 34, can be sandwiched together (or poured) in a continuous fashion so that a continuous strip of the integrated units 30, which are oriented in a side-by-side fashion, can be formed. From the assembled strip, individual units 30 can be cut or the assembled strip of units 30 can remain intact for incorporation into a cassette and/or cartridge.

In the illustrated embodiment, various adhesive layers 38, 42, 46 are used to secure the components of the integrated unit 30 together. However, it should be recognized that the components can be joined together in other manners. By way of nonlimiting examples, the components of the integrated unit 30 can be joined via adhesive tape, welding and through mechanical fasteners, to name a few.

Referring to FIGS. 1 and 2, the spacer 40 defines a capillary channel or cavity 54 through which the body fluid is collected. Spacer 40 can be formed from various materials, such as plastic, ceramic, and/or a piece of adhesive tape, to name a few. At one end, near the lancet tip 50, the capillary channel 54 has an opening 56 in which the body fluid is received. At the opposite end of the capillary channel 54, an end portion 58 encloses the capillary channel 54. In other embodiments, end portion 58 can have an opening to vent or exhaust air or other gas from the channel 54. As depicted, the capillary channel 54 is defined by end portion 58 and a pair of arms 60 that extend from end portion 58 along the vent member 36 and the lancet 32. The spacer 40 and the capillary channel 54 are sandwiched between the lancet 32 and the vent member 36, and the test strip 44. The capillary channel 54 is dimensioned to draw bodily fluid into the device 30 by capillary action. The vent member 36 is used to cover a portion of the spacer 40 and is spaced away from the lancet 32 to form a vent opening 62 from which air or other gases are vented from the capillary channel 54. The vent member 36 can be formed from various materials, such as, plastic, ceramic, and/or metal, to name a few.

The test strip 44 is positioned along the capillary channel 54 so that the test strip 44 is able to collect fluid drawn into the capillary channel 54. As illustrated in FIG. 2, the test strip 44 can analyze fluid through electrochemical means via electrodes 45 and a reagent. In this embodiment, test strip 44 is an electrochemical test strip that includes a working, counter and reference electrodes 45. It should be appreciated that test strip 44 can analyze fluid in other manners. For example, test strip 44 can analyze fluid through such means as optical (e.g., reflectance, absorption, fluorescence, RAMAN, etc.) and/or magnetic analysis to name a few.

Figure 11:
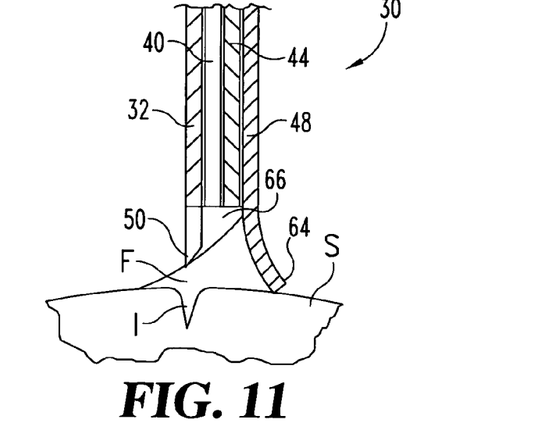
FIG. 11 is a cross sectional view of the FIG. 1 test strip during sampling of bodily fluids.

As described above, the fluid collection flag 48 is used to draw the bodily fluid sample through the opening 56 and into the capillary channel 54. With reference to FIGS. 1 and 2, the collection flag 48 has a sampling end portion 64 that contacts the droplet of body fluid and draws the fluid inside the unit 30. In one example, the flow of fluid is enhanced by forming the collection flag 48 from a hydrophilic material or coating the collection flag 48 with a hydrophilic material such as a surfactant or hydrophilic polymers. The collection flag 48 can be treated using polyamides, oxidation (e.g. corona/plasma treatment); plasma chemical vapor deposition; vacuum vapor deposition of metals, metaloxides or non-metaloxides; or deposition of an element which oxidizes with water. However, it should be understood that the collection flag can made hydrophilic in other manners. As shown, the fluid collection flag 48 is in the form of a flexible sheet. The flexibility of the collection flag 48 allows the collection flag 48 to deform or bend during lancing, and contact the skin or the body fluid droplet near the incision, as is depicted in FIG. 11. Due to the flexible nature of the hydrophilic film, the film does not significantly deform the skin when it touches the skin, and therefore, the incision in the skin remains open during collection of the fluid sample. If the fluid collection flag 48 were rigid, however, the skin may tend to deform and the incision would close, thereby cutting off the fluid supply. Moreover, with this ability to bend, the collection flag 48 is able to collect the fluid sample with the unit 30 oriented at an oblique angle relative to the skin, thereby allowing the lancet 32 to lance the skin at an oblique angle. Lancing at an oblique angle increases the number of capillaries severed when lancing at a particular depth, which in turn increases the amount of fluid. As will be appreciated, the difficulties associated with moving a capillary tube to an incision site after lancing are reduced. The ability to acquire a body fluid sample is enhanced and the loss or delay of the sample is reduced. The fluid collection flag 48 in the illustrated embodiment is transparent to allow the user to see the incision and the droplet of fluid during sampling. However, in other embodiments, the collection flag 48 can be opaque and/or semi-transparent.

Referring to FIG. 1, after the components of device 30 are assembled, they form a sampling end at opening 56 from which the lancet 32 and the sampling end portion 64 of the collection flag 48 extend. As shown, the collection flag 48 and the lancet tip 50 extend in a generally parallel relationship. As should be appreciated, the flexible collection flag 48 can bend towards or away from lancet tip 50, depending upon the orientation of device 30. As shown in FIG. 11, a gap 66 is formed between collection flag 48 and lancet tip 50 for drawing fluid F by capillary action after an incision I has been formed. In the illustrated embodiment, the sampling end portion 64 of the collection flag 48 extends past lancet tip 50 such that sampling end portion 64 can remain in contact with skin S after the lancet tip 50 is withdrawn from the incision I. In other embodiments, the sampling end portion 64 of the collection flag 48 extends to the lancet tip 50 or is shorter than the lancet tip 50.

With continued reference to FIG. 11, during lancing, collection flag 48 contacts and bends against skin S as the lancet tip 50 is driven toward the skin S. After the incision I is formed in the skin S by the lancet tip 50, the lancet tip 50 is retracted from the incision I to allow a fluid sample F to flow from the incision I. The lancet 32 can be retracted by the user or through a retraction mechanism coupled to the lancet 32. After lancing, the device 30 does not have to be repositioned or reoriented in order to collect the fluid sample F. As shown, the sampling end portion 64 contacts the skin S during fluid collection. Due to the flexibility of collection flag 48, the collection flag 48 does not substantially compress skin S such that fluid sample F from incision I is not restricted. In another embodiment, the collection flag 48 is positioned away from the skin S so as not to touch the skin S during the sampling of the fluid sample F. In this embodiment, collection flag 48 is still positioned close enough to draw fluid sample F into the opening 56 via capillary action. As mentioned previously, collection flag 48 can be optionally coated or made from a hydrophilic material for enhancing fluid flow along collection flag 48 and into opening 56. From gap 66, the fluid sample F is drawn via capillary action into capillary channel 54 and the fluid sample F is deposited on the test strip 44. The fluid sample F can then be analyzed with the test strip 44 to determine the desired property.

It was noted above that the integrated lancing test strip 30 has been constructed to minimize the size of the fluid sample. By reducing the amount of fluid needed for testing, the penetration depth of the lancet 32 can be reduced, which results in a general reduction of pain to the user. Also, the smaller sample sizes allow fluid to be collected at less vascularized locations, such as the forearm. During sampling with typical sampling devices, not all of the fluid reaches the testing area of the test strip, which results in wasting of the fluid. Sometimes the fluid can be smeared on the skin or a portion of the fluid remains in the collection device, such as a capillary tube. In the embodiments illustrated in FIGS. 3 through 10 and described below, the sampling end portion 64 of the collection flag 48 is shaped to minimize fluid waste. It was discovered that when the sampling end portion 64 of the collection flag 48 has an even rectangular shape the fluid tended to laterally wick along the edge of the flag 48 that faces the droplet before being draw into the capillary channel 54. With the lateral wicking, the drawn fluid has to generally wick along one entire surface of the collection flag 48, and a portion of the fluid remains coated over the surface of the flag 48, after the fluid is drawn into the capillary channel 54. The various shapes of the collection flag 48 in the following described embodiments minimize lateral wicking of the fluid as well as smearing of the fluid on the skin. As should be appreciated, the variously shaped collection flags 48 illustrated in FIGS. 3 through 10 are configured for use with the integrated lancing test strip 30 of FIG. 1.

Figure 3:
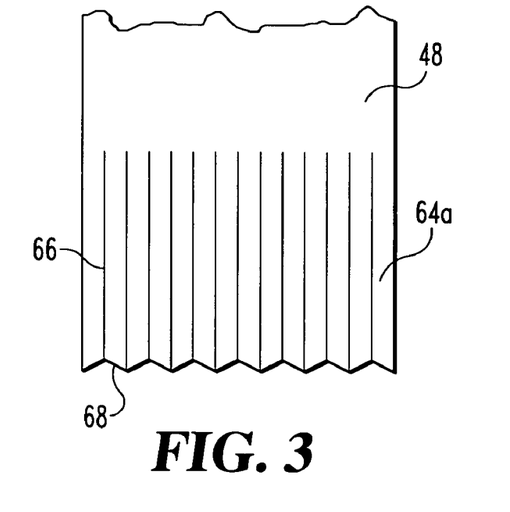
FIG. 3 is a front view of a fluid collection sheet with a fluted shape that can be used in the FIG. 1 test strip.

With the embodiment illustrated in FIG. 3, sampling end portion 64a has a fluted shape with a series of ridges or folds 66 that act to stiffen the collection flag 48 as well as minimize lateral wicking of the body fluid during sampling. The collection flag 48 is typically made of thin material that is prone, on occasion, to become permanently bent or misshapen during lancing. When the flag 48 becomes permanently bent, the flag 48 is unable to contact the droplet of fluid. The ridges 66 allow the collection flag 48 to be bent during lancing but stiffen the flag 48 in a manner to allow the flag 48 to resiliently extend to its original position after lancing. As illustrated, edge 68 of the sampling end portion 64a is angled in a zig-zag pattern, which minimizes lateral wicking of the fluid so that more of the fluid is drawn into the capillary channel 54 and is not wasted on the collection flag 48.

Figure 4:
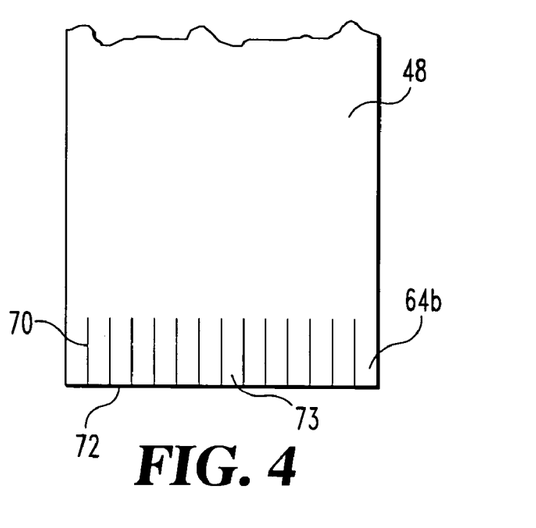
FIG. 4 is a front view of a collection sheet with a fenestrated shape can be used in the FIG. 1 test strip.

In accordance with another embodiment, sampling end portion 64a, as shown in FIG. 4, is fenestrated with a series of cuts 70 along edge 72 that create a series of tabs 73. The cuts 70 along the edge 72 minimize lateral wicking of the fluid along the edge 72 by breaking up the lateral pathways along the edge 72. As illustrated, the tabs 73 are rectangular in shape; however in other embodiments, the cuts 70 can form circular, oval, and/or trapezoidal tab shapes, to name a few. As shown, each tab 73 is the same length as the tab 73 next to it, and each tab 73 is parallel to the next one. In other embodiments, it is envisioned that selected tabs 73 can have different lengths and selected tabs 73 can be oriented relative to one other at different angles within the sampling end portion 64b.

Figure 5:
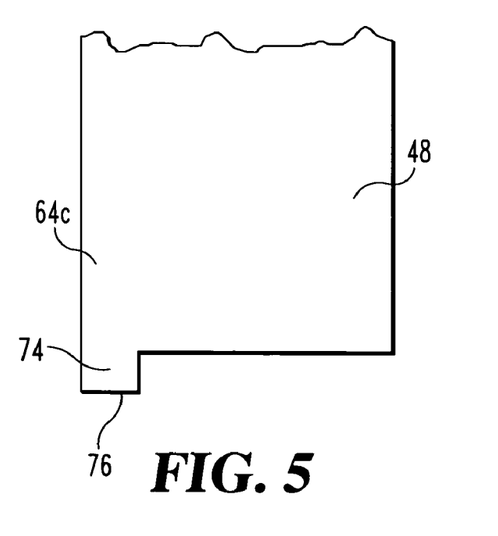
FIG. 5 is a front view of a collection sheet with a tail that can be used in the FIG. 1 test strip.

With reference to FIG. 5, sampling end portion 64c has a tail 74 with a droplet contact edge 76 that extends away from the rest of the sampling end portion. In the illustrated embodiment, the tail 74 has a rectangular shape but it should be appreciated that in other embodiments the tail 74 may be shaped differently. For example, the tail 74 can be circular, trapezoidal, or triangular, to name a few shapes. It is believed that the tail 74 maximizes the amount of fluid transferred to the capillary channel 54 by minimizing lateral wicking of the fluid. During sampling, the tail 74 initially contacts the droplet of fluid such that the fluid is only drawn via the tail 74.

Figure 6:
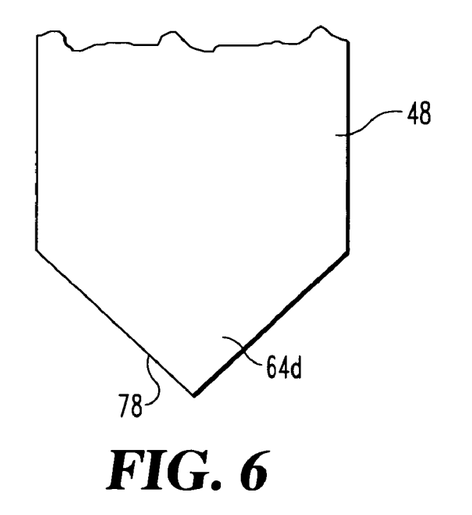
FIG. 6 is a front view of a collection sheet with a triangular shape that can be used in the FIG. 1 test strip.

Referring to FIG. 6, sampling end portion 64d has a triangular shaped edge 78 in the form of an isosceles triangle. In other embodiments, the shaped edge 78 can be angled differently. For example, the shaped edge 78 can form a right triangle, or a scalene triangle, to name a few shapes. With the triangular shaped sampling end portion 64d, a point contact is provided between the collection flag 48 and the fluid droplet so that lateral wicking along the edge 78 is reduced. Further, it was discovered that the point contact between the collection flag 48 and the droplet reduces the amount of smearing of the droplet. As mentioned before, smearing of the droplet on the skin or other tissue tends to waste body fluid.

Figure 7:
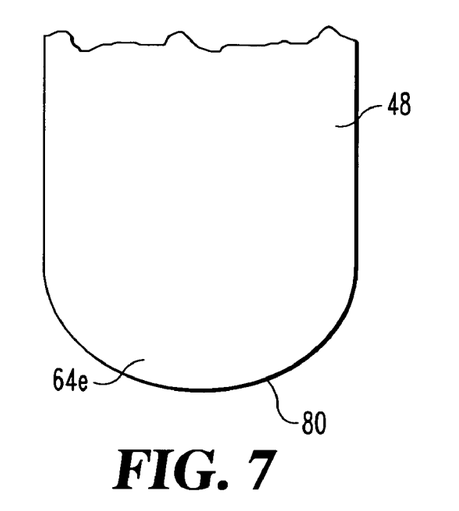
FIG. 7 is a front view of a collection sheet with a semi-circular shape that can be used in the FIG. 1 test strip.

A sampling end portion 64e according to a further embodiment is illustrated in FIG. 7. As shown, the sampling end portion 64e of the collection flag 48 has a semicircular shape with a rounded edge 80. It was found that the rounded edge 80 reduces the amount of lateral wicking of the fluid as well as smearing of the fluid droplet. In other embodiments, the rounded edge 80 can be for example oval, parabolic, or elliptical shaped.

Figure 8:
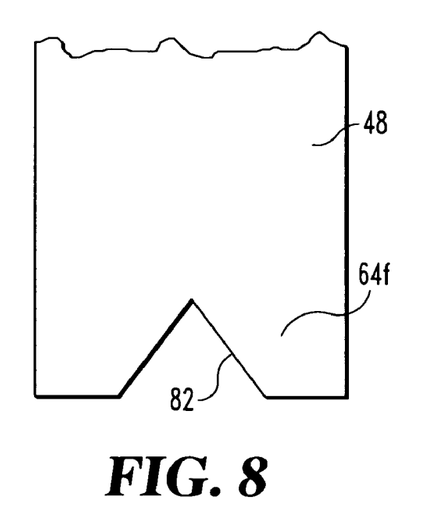
FIG. 8 is a front view of a collection sheet with a notch that can be used in the FIG. 1 test strip.

With reference to FIG. 8, the sampling end portion 64f has a notch 82 that acts as a guide to direct the fluid towards the center of the collection flag 48. Sometimes, for a number of reasons, the collection flag 48 is not centered over the droplet of body fluid. During sampling, the fluid laterally wicks along the edge of the sampling end portion 64f until the fluid reaches the notch 82, and once at the notch 82, the fluid is unable to laterally wick further so that the fluid is directed towards the center of the collection flag. In the illustrated embodiment, the notch 82 has a triangular shape, but it is envisioned that the notch 82 can be shaped differently in other embodiments. For instance, the notch 82 can have a rectangular, circular, or trapezoidal shape. It is also contemplated that the sampling end portion 64f can have multiple notches 82, and the notches 82 have different sizes and shapes relative to one another.

Figure 9:
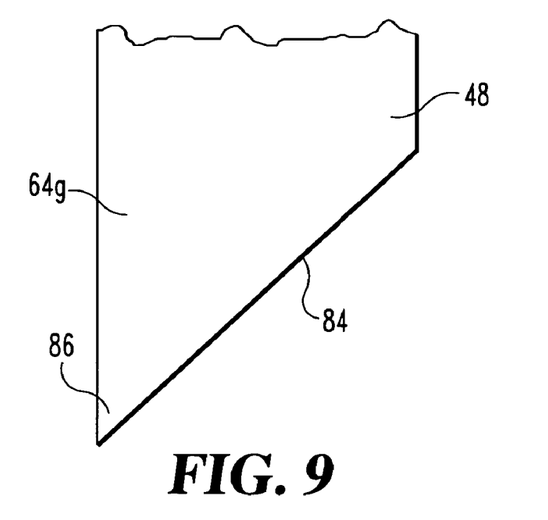
FIG. 9 is a front view of a collection sheet with an eccentric shape that can be used in the FIG. 1 test strip.

Referring to FIG. 9, a sampling end portion 64g according to another embodiment has an angled edge 84 that is in the form of a right triangle with a contact point 86. During fluid collection, the contact point 86 contacts and draws the fluid from the droplet with minimal smearing and lateral wicking. As shown angled edge 84 is straight, but in other forms, the angled edge 84 can be rounded.

Figure 10:
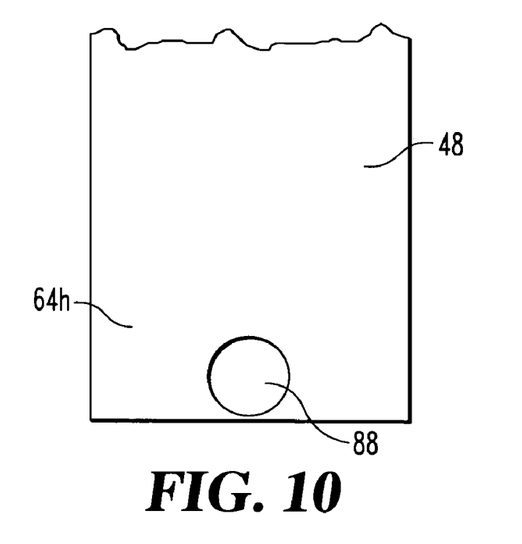
FIG. 10 is a front view of a collection sheet with a circular opening that can be used in the FIG. 1 test strip.

A sampling end portion 64h according to the embodiment illustrated in FIG. 10 defines a hole 88 that breaks up the ability of the collection flag 48 to laterally wick fluid, which in turn increases the amount of fluid transferred to the test strip 44. The hole 88 can be various shapes such as circular, rectangular, or trapezoidal, to name a few.

Figure 12:
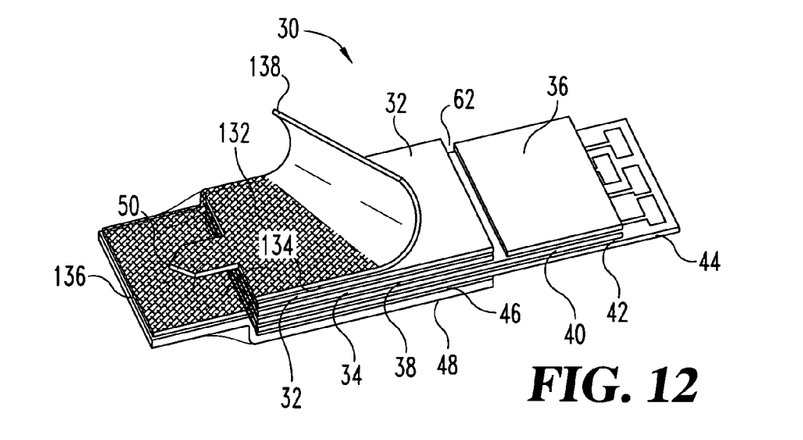
FIG. 12 is a perspective view of an integrated test strip according to another embodiment of the present invention.

An integrated sampling device 30 according to another embodiment of the present invention is illustrated in FIG. 12. Device 30 has many components that are similar to device 30 illustrated in FIGS. 1 and 2, with notable exceptions described below. Like the previous embodiment, device 30 is configured to lance an incision into the skin and draw fluid from the incision into a capillary channel via a collection flag 48.

It is envisioned that in other embodiments, the collection flag 48 can be treated or made with hydrophobic and/or hydrophilic to create areas that correspond in shape to the above described shapes of the collection sheet 48. For example, a triangular area of hydrophilic material can be formed on the collection flag 48 in order to reduce lateral wicking of the fluid. Also, it is contemplated that hydrophilic/hydrophobic areas can be used in conjunction with specifically shaped collection flags 48 so as to reduce lateral wicking and further define the fluid flow path.

Maintaining the sterility of the integrated lancing test strip 30, especially the lancet 32, is always a concern. If the lancet 32 is contaminated, infection or other serious injuries can result. In FIG. 12, the integrated lancing test strip 30 has a protective film 132 that, along with the collection flag 48, is configured to cover and maintain the sterility of the tip 50 of the lancet 32. The film 132 has a lancet engaging surface 134 for securing the film 132 to the lancet 32. The lancet engaging surface 134 is coated with an adhesive, such as a low tack adhesive, which has a low bond strength for metal. The lancet engaging surface 134 coated with adhesive is placed over the lancet 32 and lancet tip 50. The lancet engaging surface 134 further adheres to the collection flag 48 as it covers the lancet 32 and the lancet tip 50.

Once the lancet tip is sterilized, the film 132 is applied over the lancet 32 and is bonded to the collection flag 48. In one embodiment illustrated in FIG. 12, the film 132 can cover the lancet 32 and form a seal 136 with the collection flag 48 around the lancet tip 50. In this form, the entire lancet engaging surface 134 is coated with an adhesive. In another embodiment illustrated in FIG. 13, a portion of the lancet engaging surface 134 is coated with an adhesive such that the adhesive does not cover the lancet tip 50 as the film 132 is placed over the lancet 32 to form seal 136 with collection flag 48 around lancet tip 50. In either embodiment, film 132 provides a moisture free environment or a pocket around the lancet tip 50 while the film 132 covers the lancet 32 and forms a seal 136 with the collection flag 48. Together, the film 132 and the collection flag 48 protect the lancet 32 and the lancet tip 50 from damage prior to use. Additionally, the seal 136 formed from film 132 and collection flag 48 protects others from accidental pricking of the lancet tip 50.

Figure 13:
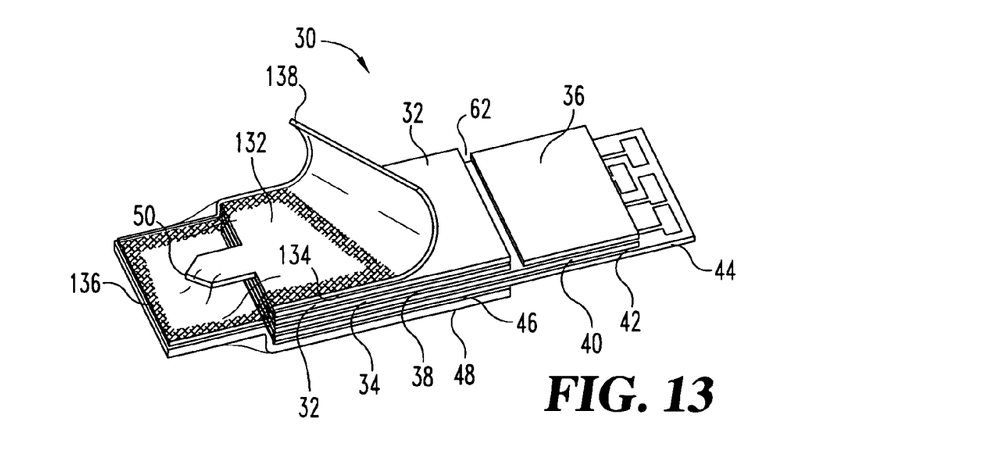
FIG. 13 is a perspective view of an integrated test strip according to yet another embodiment of the present invention.

In both illustrated embodiments, the film 132 has an end region 138 that is not coated with an adhesive. The end region 138 provides an adhesive free area for the user or a mechanical device to more easily grasp and remove the film 132 to expose the lancet 32. The film 132 is removed by grasping the end region 138 and peeling the film 132 from the lancet 32, while the collection flag 48 remains attached to the test strip 44. As should be appreciated, the flexibility of the film 132 and the type of adhesive used on the film 132 allow the film 132 to be easily removed from the lancet 32 and the collection flag 48.

It is contemplated that in other embodiments the integrated lancing test strip 30 can have a pair of films 132 such that the lancet engaging surface 134 of each pair of films 132 is coated with an adhesive. Further in this embodiment, one of the films 132 is placed over the lancet 32 and the lancet tip 50. The other film 132 is placed over the test strip 44 such that it extends from the test strip 44 and the lancet engaging surface 134 covers the lancet 32 and lancet tip 50. The lancet engaging surfaces 134 attach to each other to surround the lancet tip 50 and form a seal. In one form, the collection flag 48 is not part of the embodiment encompassing a pair of films 132. However, in another embodiment, the pair of protective films 132 are in the form of a pair of fluid collection flags 48 that remain attached to the integrated unit 30. Before use, the pair of fluid collection flags 48 are pulled apart, either manually or automatically, so that the lancet tip 50 is exposed, and once the incision is formed, both collection flags 48 are used to draw fluid onto the test strip 44.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An integrated bodily fluid sampling device for sampling a bodily fluid from an incision in skin, comprising:
   a lancet having a lancet tip for forming the incision in the skin;
   a test strip attached to the lancet for analyzing the bodily fluid from the incision, the lancet being fixed to the test strip;
   a fluid collection flag having a sampling end portion extending from the test strip for drawing the bodily fluid onto the test strip, the sampling end portion is at least as long as the lancet, the collection flag being flexible to bend against the tissue during lancing wherein the collection flag is resilient to maintain the shape of the collection flag after contact with the tissue, the sampling end portion having a structure to minimize lateral wicking of the bodily fluid; and
   a protective film detachably coupled to the fluid collection flag for protecting at least the lancet tip, wherein the lancet tip is sandwiched between and contacts both the fluid collection flag and the film.

2. The device of claim 1, wherein the fluid collection flag is coated with a hydrophilic material.

3. The device of claim 1, wherein the protective film includes a lancet engaging surface coated with an adhesive material to cover the lancet.

4. The device of claim 3, wherein the lancet engaging surface includes an end region without adhesive material.

5. The device of claim 1, wherein the protective film and the fluid collection flag form a seal for surrounding the lancet tip.

6. The device of claim 1, wherein the structure is a fluted shape.

7. The device of claim 1, wherein the structure is a fenestrated shape.

8. The device of claim 1, wherein the structure is a tailed shape.

9. The device of claim 1, wherein the structure is a triangular shape.

10. The device of claim 1, wherein the structure is a semicircular shape.

11. The device of claim 1, wherein the structure is a notched shape.

12. The device of claim 1, wherein the structure is a tapered shape.

13. The device of claim 1, wherein the structure is a rectangular shape defining a hole near an edge.

14. The device of claim 1, further comprising:
a spacer defining a capillary channel, the spacer sandwiched between the lancet and the test strip; and
the fluid collection flag located exteriorly of the capillary channel.

15. The device of claim 1, wherein the test strip is sandwiched between the lancet and the fluid collection flag.

16. The device of claim 1, wherein the fluid collection flag is transparent to permit viewing of the incision.

17. The device of claim 1, wherein:
the test strip includes an electrode; and
an insulating layer covers a portion of the lancet, wherein the insulating layer prevents electrical interference between the lancet and the electrode.

18. The device of claim 17, wherein the insulating layer includes aluminum oxide.

19. The device of claim 17, wherein the insulating layer includes polyparaxylene.

20. The device of claim 17, wherein the insulating layer includes polymer.

21. The device of claim 1, wherein the protective film is permanently attached to the device to form a second fluid collection flag.

22. A device for sampling a body fluid from an incision in skin, comprising:
a lancet having a lancet tip to form the incision in skin;
a test strip coupled to the lancet for analyzing the body fluid from the incision; and
a flexible fluid collection flag having a sampling end portion for drawing the body fluid to the test strip, the fluid collection flag attached to the test strip wherein the sampling end portion extends from the test strip, the sampling end portion having a fluted shape with a plurality of ridges that enable the sampling end portion to bend against the skin during lancing, wherein the ridges stiffen the collection flag to allow the collection flag to resiliently extend to its original position after lancing when the lancet tip is retracted from the incision.

23. The device of claim 22, wherein the fluid collection flag is coated with a hydrophilic material.

24. The device of claim 22, wherein the fluid collection flag is transparent to permit viewing of the incision.

25. The device of claim 22, further comprising:
the lancet and the sampling end portion define a gap configured to draw the bodily fluid onto the test strip by capillary action.

26. The device of claim 22, wherein:
the test strip includes an electrode; and
an insulating layer covers a portion of the lancet, wherein the insulating layer prevents electrical interference between the lancet and the electrode.

27. The device of claim 22, wherein:
the sampling end portion includes an edge angled in a zig-zag shape to minimize lateral wicking of body fluid along the length of the fluid collection flag.

28. The device of claim 22, further comprising:
a protective film detachably coupled to the fluid collection flag, wherein the protective film and the fluid collection flag form a seal for surrounding the lancet tip.

29. The device of claim 28, wherein the lancet tip is sandwiched between and contacts both the fluid collection flag and the protective film.

30. The device of claim 28, wherein the protective film is permanently attached to the device to form a second fluid collection flag.

31. The device of claim 28, wherein the protective film includes a lancet engaging surface coated with an adhesive material to cover the lancet.

32. The device of claim 31, wherein the lancet engaging surface includes an end region without adhesive material.

33. A device for sampling a body fluid from an incision in skin, comprising:
a lancet having a lancet tip to form the incision in skin;
a test strip coupled to the lancet for analyzing the body fluid from the incision, the lancet being fixed to the test strip; and
a flexible fluid collection flag having a sampling end portion for drawing the body fluid to the test strip, the fluid collection flag attached to the test strip wherein the sampling end portion extends from the test strip and extends past the lancet tip, the sampling end portion having a fluted shape with a plurality of ridges that enable the sampling end portion to bend against the skin during lancing, wherein the ridges stiffen the collection flag to allow the collection flag to resiliently extend to its original position after lancing when the lancet tip is retracted from the incision.

34. A device for sampling a bodily fluid from an incision in tissue, comprising:
a lancet having a lancet tip to form the incision in the tissue;
a test strip attached to the lancet for analyzing the bodily fluid from the incision, the lancet being immovable with respect to the test strip; and
a fluid collection flag having a sampling end portion for drawing the bodily fluid to the test strip, the fluid collection flag attached to the test strip wherein the sampling end portion extends from the test strip and is at least as long as the lancet, the collection flag being flexible to bend against the tissue during lancing wherein the collection flag is resilient to maintain the shape of the collection flag after contact with the tissue, the sampling end portion having a fenestrated shape to minimize lateral wicking of the bodily fluid, wherein the fenestrated shape includes a plurality of slits in the sampling end portion.

35. The device of claim 34, wherein the fluid collection flag is coated with a hydrophilic material.

36. The device of claim 34, wherein the fluid collection flag is transparent to permit viewing of the incision.

37. The device of claim 34, wherein:
the test strip includes an electrode; and
an insulating layer covers a portion of the lancet, wherein the insulating layer prevents electrical interference between the lancet and the electrode.

38. The device of claim 34, further comprising a protective film detachably coupled to the lancet.

39. The device of claim 38, wherein the protective film includes a lancet engaging surface coated with an adhesive material to cover the lancet.

* * * * *